United States Patent [19]

Zuckerman

[11] 4,423,407
[45] Dec. 27, 1983

[54] APPARATUS AND METHOD FOR MEASURING THE CONCENTRATION OF GASES

[75] Inventor: Matthew Zuckerman, Carmel, Calif.

[73] Assignee: Dart Industries, Inc., Colmar, Pa.

[21] Appl. No.: 238,768

[22] Filed: Feb. 27, 1981

[51] Int. Cl.³ .............................................. H01L 7/00
[52] U.S. Cl. ........................................ 338/34; 422/98
[58] Field of Search .................. 338/34, 35; 73/27 R; 422/98; 252/512–515, 518–520

[56] References Cited

U.S. PATENT DOCUMENTS

| | | | |
|---|---|---|---|
| 3,092,799 | 6/1963 | Baker | 337/34 |
| 3,428,892 | 2/1969 | Meinhard | 324/71 |
| 3,479,257 | 11/1969 | Shaver | 23/232 R X |
| 3,550,057 | 12/1970 | Young | 338/34 |
| 3,564,474 | 2/1971 | Firth | 338/25 |
| 3,564,476 | 2/1971 | Barden | 338/174 |
| 3,578,409 | 5/1971 | Silverman | 338/34 X |
| 3,611,243 | 10/1971 | Hardtl | 338/34 |
| 3,732,519 | 5/1973 | Taguchi | 338/34 |
| 3,793,605 | 2/1974 | Fehiner | 338/34 |
| 3,820,958 | 6/1974 | Cheng | 338/34 X |
| 3,865,550 | 2/1976 | Bett | 338/13 X |
| 3,872,419 | 3/1975 | Groves | 338/25 |
| 3,891,958 | 6/1975 | Wakabayashi | 338/35 |
| 3,900,815 | 8/1975 | Taguchi | 422/98 X |
| 3,911,386 | 10/1975 | Beaudein | 338/34 |
| 3,924,219 | 12/1976 | Brown | 338/34 |
| 3,951,603 | 4/1976 | Obayashi | 338/34 X |
| 3,953,173 | 4/1976 | Obayashi | 338/34 X |
| 3,959,764 | 5/1976 | Allman | 335/34 |
| 3,970,431 | 7/1976 | Wise | 338/34 X |
| 3,973,192 | 8/1976 | Justi | 338/34 X |
| 3,999,947 | 12/1976 | Mihara | 338/34 X |
| 4,001,756 | 1/1977 | Heijne | 338/34 |
| 4,001,757 | 1/1977 | Sato | 338/34 |
| 4,011,538 | 3/1977 | Froemel | 73/27 R X |
| 4,012,709 | 3/1977 | Logothetis | 338/34 |
| 4,016,308 | 4/1977 | Frazee | 252/519 X |
| 4,016,524 | 4/1977 | Pompei | 338/34 |
| 4,017,792 | 4/1977 | Heiland | 338/34 X |
| 4,017,820 | 4/1977 | Ross | 338/35 |
| 4,039,941 | 8/1977 | Morrison | 338/34 X |
| 4,045,764 | 8/1977 | Ichinose | 338/34 |
| 4,058,368 | 11/1977 | Svensson | 73/23 X |
| 4,067,695 | 1/1977 | Miyaguchi | 338/34 X |
| 4,072,467 | 2/1978 | Jones | 338/34 X |
| 4,077,775 | 3/1978 | Lacroix | 338/34 |
| 4,086,556 | 4/1978 | Nitta | 338/35 |
| 4,130,797 | 12/1978 | Hattori | 338/34 X |
| 4,147,513 | 4/1979 | Bienkowski | 338/34 X |
| 4,151,503 | 4/1979 | Cermak | 338/14 |
| 4,172,247 | 10/1979 | Ikeura | 338/34 |
| 4,187,486 | 2/1980 | Takahashi | 338/34 |
| 4,241,019 | 12/1980 | Nakatani et al. | 338/34 X |
| 4,265,844 | 5/1981 | Yokomizo et al. | 338/20 X |
| 4,338,223 | 7/1982 | Yokomizo et al. | 338/21 X |
| 4,343,768 | 8/1982 | Kimura | 422/98 X |

FOREIGN PATENT DOCUMENTS 55-78235  6/1980  Japan .................. 338/34

*Primary Examiner*—C. L. Albritton
*Attorney, Agent, or Firm*—Amster, Rothstein & Engelberg

[57] ABSTRACT

A gas sensing apparatus is adapted to detect the presence of a gas of interest in air in very small quantities and to provide a rapid alarm or other indication in response to the presence of such gas. The apparatus incorporates a gas sensing composition which changes its electrical resistance more dramatically than previously possible in response to the presence of the gas and electronic circuitry designed to sense and evaluate the patterns of resistance change during the first approximately 30 seconds after exposure to gas and to accurately estimate gas concentration based on such initial resistance variations. The system also looks at overall change in sensor resistance to detect gradually increasing gas levels. A preferred method of manufacturing the sensor and a sensor configuration particularly suited to the early detection of gas levels are disclosed.

16 Claims, 9 Drawing Figures

APPARATUS AND METHOD FOR MEASURING THE CONCENTRATION OF GASES

This invention relates generally to apparatus and methods for monitoring the concentration of gases in air employing gas sensitive materials which change electrical characteristics in response to the presence of a gas of interest.

There is a great and ever increasing need in industry for apparatus which is capable of quickly sensing the presence of relatively small quantities of unwanted gases in air and providing an alarm or other indication of the presence of such gas. Many industrial facilities operate under circumstances where escape of toxic gas which may cause short or long term health hazards is an ever present danger. Government regulations now provide maximum safe ambient levels for approximately 400 gases. The ability to detect such gases in the environment quickly and in very small concentrations may be a crucial factor in permitting timely responsive action.

In the past, a variety of gas sensor systems have been developed. For many years, such systems have incorporated electrical circuits which employ a gas sensitive electrical element adapted to change electrical characteristics in response to the presence of various gases. The measurement of the concentration of gases in air by changes in electrical properties of sensing elements first was done in the early 1930's. The first task was to measure conbustible gas such as methane to determine whether the gas to air mix was near the point at which an explosion might occur. This was accomplished by use of a heated platinum wire which would on exposure to air and gas catalize combustion and raise its temperature, changing its resistance. Later sensors were designed to get less drift in baseline response and higher signal level. These sensors involved differently shaped coil configurations.

Another class of sensors for combustible gas was developed using metal and metallic oxides. These sensors produced a substantial signal, but had a substantial drift of the baseline signal level on repetitive exposure to gas and had a memory of the previous exposure.

Toxic gases such as hydrogen sulfide and chlorine then became of interest and sensors to measure these gases were made of other metal-metal oxide complexes.

Initially toxic gas sensors were coils of wire fabricated of gas sensitive materials. However, sensors of this general type have suffered from a number of serious drawbacks. For example, changes other than changes in the concentration of the subject gas seriously affect the electrical resistance of the sensor including, for example, changes in temperature or humidity. While attempts have been made to overcome this drawback by operating at elevated temperatures or incorporating other temperature compensating devices, the results have not been entirely satisfactory. In addition, electrical sensors of this type respond to gas relatively slowly and suffer from uncertainties resulting from the long term aging of the sensor which, over a period of time, alters its normal characteristics.

In more recent years, metal oxide semi-conductor type materials have been placed on hybrid substrates for use as gas sensors. These semi-conductor materials also change resistance in response to the presence of various gases. However, sensors of this type are characterized by uncertainty in their initial resistance value and the degree of resistance change they exhibit varies widely from sensor to sensor, even in the same production lot. Further in sensors of this type, repetitive exposure to the object gas tends to condition the sensors, resulting in non-reproducible resistance change on repetitive gas exposures.

Also significant is the fact that the response of such prior sensors on exposure to the desired gas is progressive and takes a relatively substantial period of time to reach an equilibrium condition reflective of the actual gas concentration. Similarly, when the object gas is removed and the sensor is exposed to a plain air environment, such sensors tend toward their normal operating resistance relatively slowly. These sensors are thus subject to substantial drift of their nominal base line signal level, particularly on repetitive exposure to gas.

Until now, such semi-conductor sensors have relied on the cumulative amount of resistance change of the sensor as the basis for an instrumented method for monitoring the concentration of gas. The composition, physical configuration and monitoring techniques associated with such sensors have been guided by such reliance. Applicant has found that highly improved sensors can be created which exhibit more marked changes in resistance than previously possible and which permit a monitoring system to focus on rates and patterns of resistance change, as well as the absolute value of change. By designing sensor compositions and configurations to emphasize such rates and patterns of change, particularly during the period immediately following exposure of the sensor to the gas of interest, applicant is able to detect gas more quickly and accurately than previously possible.

It is thus an object of the present invention to create a gas-sensing system which indicates the presence of even low levels of a subject gas in the environment more quickly and more accurately than previously possible. It is an object of the present invention that the response of such system be highly reproducible, even as the system ages and even in the face of repeated exposure to the subject area. A further object of the invention is to develop a sensing system which quickly returns to nominal values when the sensor returns to an air environment and one which provides an indication of various pre-established gas levels, giving different alarms in response to different concentrations.

In accomplishing these and other objects, the present invention incorporates a gas-sensing composition and a mechanical configuration which provides a sharp and dramatic resistance change in response to the presence of even low concentrations of gas. Applicant's device incorporates monitoring circuitry which senses and interprets the early patterns of change of resistance to provide a quick indication of the presence and concentration of the gas in question.

Applicant's resistance element is preferably a porous mass of metal and metal oxide, in which the metallic form (as opposed to the oxide form) predominates, preferably with additional constituents. The sensor may also comprise a very thin film of the same sensing material. In either case, the composition and configuration of the sensor element is adapted to have a very high surface to mass ratio to emphasize the materials' surface sorption reaction with the subject gas and to de-emphasize the slower chemical reaction between the sensor and the gas.

The physical configuration and support structure of the sensing material is characterized by a relatively short strip of the sensor material deposited between a pair of conductive pads mounted over a heater resistor of relatively larger dimension.

The sensing material is preferably fabricated in situ using the heater resistor to generate rather high manufacturing temperatures. The material composition and temperature profile are designed to create a very high porosity to provide a large surface area to mass ratio, thus emphasizing the surface phenomena which are believed to provide the most rapid initial resistance changes. As an alternative, a very thin film of the sensing material having a high surface to mass ratio can be employed.

The resistance of the composition is preferably monitored as the sensing material is formed through its heating cycle and the heating cycle is controlled and terminated in partial dependence on the measured resistance of the material.

During operation, the heater resistor provides uniform heat of the sensing material at operating temperatures chosen to emphasize the sorption reaction over the chemical reaction in both directions.

The electrical sensing circuitry associated with applicant's gas sensor is devised to be sensitive to the patterns of initial rapid change in resistance of the sensor material, from which it can accurately predict concentration of the gas in question. The circuitry looks principally at the slope of the sensor signal change by focusing on the derivative of the sensor signal with a time constant in the order of 1-15 seconds so that slow, progressive changes due to sensor aging, temperature change and other similar phenomena are eliminated. Additionally, other portions of the circuitry focus on the long term variation of the signal level to detect very slow increases in gas concentration as could be caused by slow leak type phenomena.

Further objects, features and advantages of the present invention will be better understood by reference to the following detailed description of a presently preferred embodiment of the invention when taken in conjunction with the appended drawings wherein.

Figure 1:
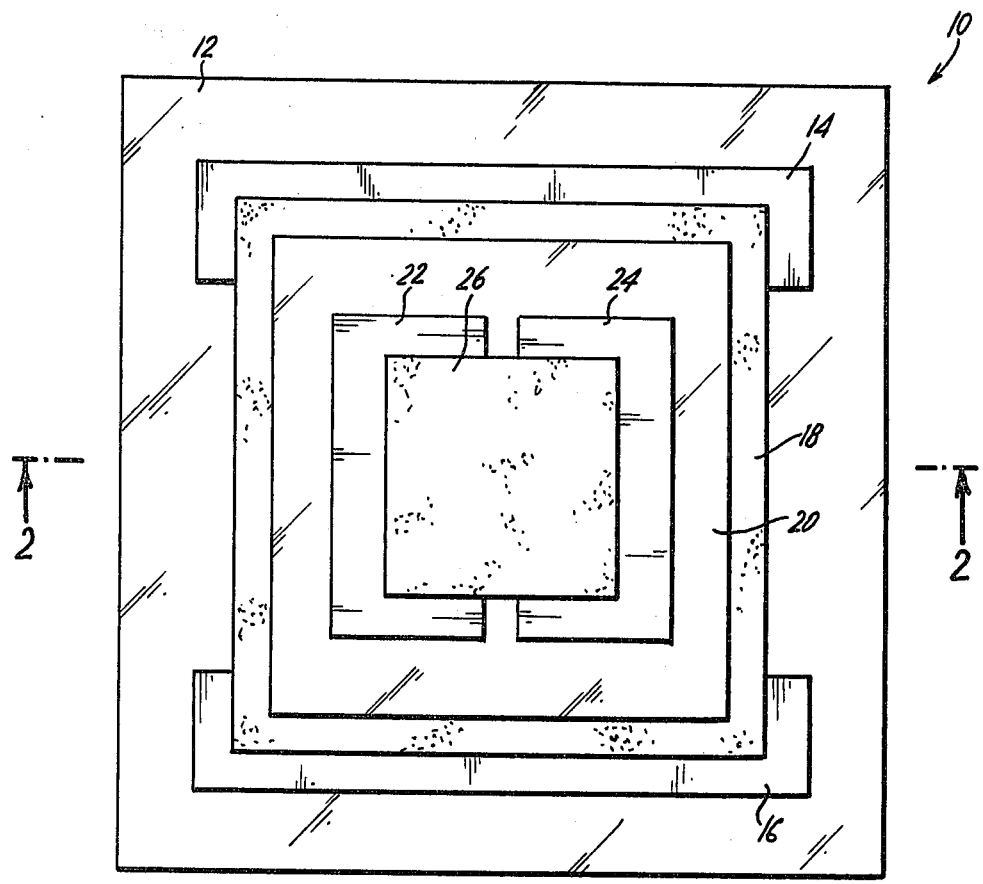
FIG. 1 is a plan view of a preferred sensor configuration in accordance with the present invention.

Prior metal oxide or semi-conductor type gas sensors produce a resistance change in response to the presence of an object gas. However, such sensors return to their initial resistance only after long exposure to an atmosphere without the subject gas. It is believed that in such prior sensors, the gas and sensor material combine to form a metal gas compound which decomposes in the presence of a normal atmosphere only after a relatively long period of time. The reversal of this chemical reaction requires a high activation energy creating a need for high operating temperatures or a purge system which raise the temperature of the sensor to a relatively high level after exposure. Indeed, some of the compounds formed may never decompose, leaving a permanent change in the sensor's resistance.

Contrary to the traditional semi-conductor sensor, the composition of applicant's sensor and the processing for its manufacture are designed to focus on the surface sorption of the object gas on the surface of the sensor and to reduce, as far as possible, reliance on the chemical reaction of the gas with the body of sensor material. Typically of the sorption process the gas which remains in the gas phase associates with the metal in the solid phase affecting its localized electrical resistance.

Applicant's sensor is a combination of metal and metal oxide with the metal phase predominating, formulated in a configuration which emphasizes a high surface to mass ratio, such as a highly porous mass or a very thin film.

Applicant's sensor may preferably also include a metal gas compound which would normally be the end product of a chemical reaction between the subject gas and the metal in the sensor. This metal gas compound exists in applicant's sensor throughout the depth of the sensor material and not just at the sensor surface. The initial presence of this compound provides a reverse concentration driving force that minimizes the signal associated with chemical reaction of the gas and metal, for given gas concentrations, and aids quick recovery when the gas is removed.

In addition, applicant's sensor may include a stable, inert material such as alumina, which helps support the porous sensor mass in its final form.

The principles of the present invention will be more readily appreciated in the context of a specific gas and sensing composition such as chlorine gas.

In the preparation of a sensor in accordance with applicant's invention for chlorine gas, applicant employs a composition of tin and its oxide forms, in which tin dominates in the sensor element. Stannic chloride may be advantageously employed in small quantities as a composition of the tin and object gas. The initial composition from which the sensor is formed also preferably includes a material such as aluminum nitrate which, as the sensor is heated in air, forms alumina as a stable, inert material to establish the sensor mass.

In accordance with applicant's invention, a chlorine sensor is formed by mixing appropriate proportions of finely divided elemental tin, stannic chloride, stannous oxide and aluminum nitrate in a water slurry. The dry materials may be composed as follows:

| Material | Preferred | Range |
| --- | --- | --- |
| Stannic Chloride | 5% | 2-15% |
| Aluminum Nitrate with 9 H$_2$O | 10% | 5-20% |
| Elemental Tin | 75% | 50-95% |
| Stannous Oxide | 10% | 5-20% |

The elemental tin is finely divided, preferably in a small enough particle size to pass a 325 mesh. The percentages given above are weight percentages of the dry materials to which water is added to form the slurry. As an example, the composition may be formed by mixing 0.695 grams stannic chloride, 1 gram aluminum nitrate with 9 H$_2$O, 7.5 grams finely divided elemental tin, 1 gram stannous oxide in a slurry with 2 c.c. water.

The slurry composition is then air dried and processed through a heating cycle to form a highly porous mass containing tin and tin oxide with the metallic phase predominating, along with stannic chloride as a dopant, all in a porous mass supported by alumina formed from the aluminum nitrate during heating.

It should be understood that in lieu of the water slurry and formation of a porous mass, a very thin film of the metal, metal oxide and preferably metal gas compound can be formed.

In accordance with applicant's invention, the gas sensitive material is preferably formed in situ on a mechanical structure which provides both for the heating of the composition in manufacture and for the maintenance of proper operating temperatures when the sensor is in use. To this end, applicant has devised a gas sensor structure generally designated by the numeral 10 in FIGS. 1 and 2 in which the heater element and the sensor element are electrically isolated but in thermal communication. This structure is desgned to permit the use of high manufacturing temperatures well in excess of those possible with imbeded coils, which tend to form an amalgam with the sensor material destroying the heating coil at high temperatures.

Structure 10 includes a support substrate 12 of insulating material such as silica. On this substrate is deposited two thick film conductive pads 14 and 16, preferably of gold material 4/9ths pure. A thick film resistor 18 is deposited between the conductive pads 14, 16 on the substrate. In the preferred embodiment, this resistor is trimmed to within 1% of 40 ohms. As indicated previously, this resistor operates as a heater element in the formation of the gas-sensitive mass and for maintaining operating temperature when the sensor is in use. Thick film resistance compositions suitable for this purpose are well known in the art and need not be described here in detail.

Above resistor 16 is a dielectric insulating material 20. Applicant has found that two layers of screen printed alumina material are suitable. These layers are preferably formed by depositing an alumina forming paste, firing it, depositing a second layer of such paste and firing again. Various screen printable dielectric materials suitable for this purpose are well known in the art and will not be described here in detail.

The layer of dielectric material provides a surface for the deposit and functioning of the gas sensor material. Dielectric 20 electrically insulates the resistor 18 from the sensing element which will be deposited on the top surface of the dielectric, while allowing the sensing element to be heated from beneath by heater resistor 18. Two gold conductive pads 22, 24 are deposited on top of the dielectric layer 20, with the gap between the two pads on the surface of the dielectric layer providing the receiving area for the gas sensing material. The gap between conductive pads 22 and 24 is preferably made relatively small. It is kept small so that the gas can diffuse quickly and completely throughout the porous mass and reach all accessible surface area quickly. It is also small with respect to the area of the heater resistor so that the heater resistor heats the sensor material in a relatively uniform manner. Typical spacing for the gap between pads 22 and 24 would be less than four mils, with a gap of approximately two mils being preferred for the tin, tin oxide chlorine sensor. The spacing of the gap is also selected so as to produce a desired resistance through the sensor material, preferably in the range of 500 to 20,000 ohms.

As indicated above, the present heater structure makes possible the establishment of much higher temperatures for manufacture of the sensor material in situ than are possible with imbeded coil-type heaters.

Appropriate electrical connections (not shown) are made to the heater resistor pads 14, 16 and separate electrical connections are provided for the sensor pads 22, 24. Methods for the attachment of appropriate leads to these pads are well known in the art and will not be described in detail. The leads to the heater resistor are connected to an appropriate electrical supply of a type well known in the art while the leads to the sensor element pads are connected to an electrical circuit for sensing change in the sensor.

The sensor chip is preferably bound by a high temperature cured epoxy or other suitable material to a header such as a t05 header of the type normally used for hybrid elements. This header provides a heat sink which, on exposure to gas, may provide additional available thermal energy to the sensor so that thermal energy requirements do not limit the reaction of the sensor on exposure to gas. The overall sensor is intended to be attached within a head assembly (not shown) of a type well known in the art. The head assembly is adapted to provide easy and free access of environmental atmosphere to the sensor, preferably filtering out dust.

The sensor element 26 is formed in situ in the gap between pads 22 and 24 by a procedure adapted to maintain the predominantly metallic character of the material and to form the sensor as a highly porous mass. Substantial porosity and a high surface area to mass ratio is important in that the sorption reaction which is the reaction believed responsible for the rapid initial change in resistance focused on by the monitoring system is essentially a surface phenomenon.

In the formation of the chlorine gas sensor, the water slurry of tin, stannous oxide, stannic chloride and aluminum nitrate is deposited in the gap between pads 22, 24. The slurry is then air dried before further processing.

In one significant aspect of applicant's invention, the resistance of the sensing material is monitored during the manufacturing phase to determine, in part, the timing of the heating cycle used in manufacturing the sensing element. During this manufacturing phase, the heater resistor is supplied from an appropriate source of electrical power and the sensor pads are connected to appropriate equipment to measure resistance.

Figure 2:
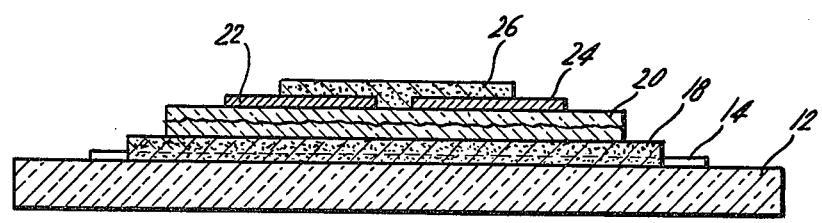
FIG. 2 is a cross-sectional view taken along line 2—2 in FIG. 1.
Figure 3:
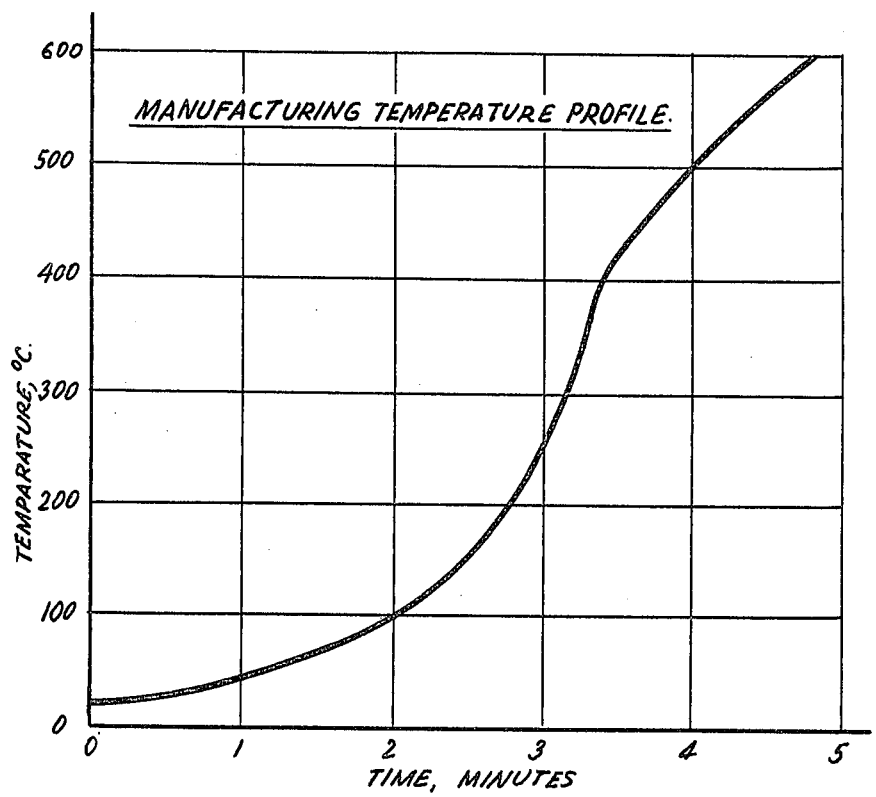
FIG. 3 is a graphic representation of the approximate temperature change of the sensor material during manufacture resulting from the voltage profile of FIG. 4.

When the water slurry described above is deposited in the gap between pads 22, 24 in FIG. 1, the resistance of the material, when cool, starts at in excess of 20 megaohms. Voltage is applied across the heater resistor (having a nominal resistance of 40 ohms) with a relatively constantly increasing voltage as shown in the time voltage profile of FIG. 4. This profile produces a temperature profile approximately as shown in FIG 3. Heating is conducted in a normal air atmosphere.

As the element is heated, the tin melts (at 231° C.) and islands of tin are formed in the gap. The tin also forms an amalgam with the gold at the conducting pads forming an electrically communicative bond. As the temperature increases, various oxide forms of tin are created. As the sensor mass is heated, the resistance of the mass decreases.

If heating proceeded over a long enough time, it would be expected that the resistance of the sensor would first decrease as conductive islands of metal are formed through the mass. The mass would reach a minimum resistance, after which the resistance would increase as the conductive metal converted to its oxide form. Stated differently, during the first phase of heating, the formation of metallic conductive paths in the material predominates. Thereafter, with continued temperature and time, the oxidation phase predominates and the resistance would rise again.

As indicated previously, it is an objective of the present invention to have the sorption reaction between the gas and sensor dominate the monitored changes in resistance of the sensor. This leads to the desire for more tin than oxide, with the presence of oxide as a dopant to bring resistance of the film into a convenient resistance range. To achieve this purpose, during the manufacturing phase of the sensor as described above, the change in resistance of the sensor with time is monitored as the sensor film is heated and the heating process is halted before the minimum of the resistance profile is reached. This timing precludes the formation of excessive metal oxide in the composition.

Alternate methods of controlling the formation of oxide in the material will be apparent to those skilled in the art. For example, the atmosphere of firing can be controlled to limit oxygen. Alternatively, the voltage on the heater resistor can be decreased at a selected point to maintain a constant temperature at a desired level so that oxidation proceeds at a slower rate.

Figure 4:
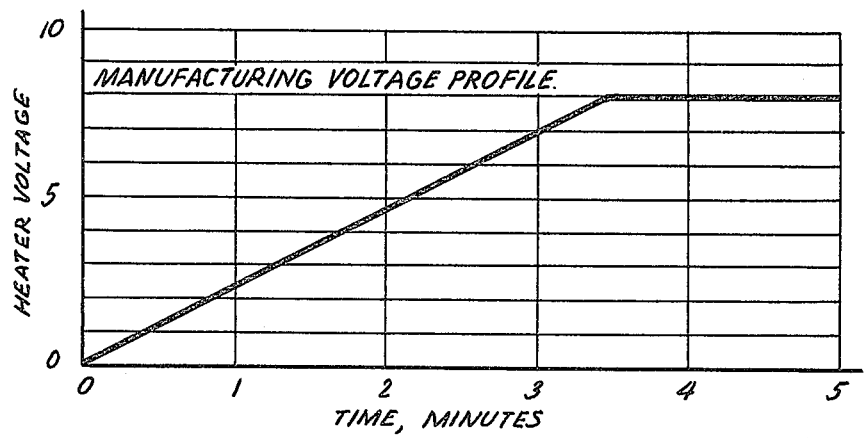
FIG. 4 is a graphic representation of heater voltage versus time in a preferred manufacturing cycle for applicant's sensor.

As indicated in FIG. 4, the voltage across the heater resistor is preferably increased at a relatively constant rate until a point is reached and thereafter maintained constant. The constant voltage is started when the film resistance, as measured during the manufacturing cycle, falls below a selected resistance. Thereafter, the heater voltage is maintained at a constant value until the film resistance reaches a second selected resistance, at which point the voltage is decreased over a 15–30 second interval to zero. In the case of the chlorine sensor described above, the first resistance at which the constant voltage is begun is one megaohm and the second resistance at which heating is terminated is preferably 1,000 ohms.

Analyses of multiple samples using the slurry described above in the physical configuration described above and the heating cycle shown in FIGS. 3 and 4 indicates a concentration of tin in the final sensor of preferably approximately 70% and preferably in a range of 50–95%.

An objective of the sensor formulation is to provide a substantial surface area compared to the mass of the sensor and to minimize the distance that the gas must travel to come in contact with the mass of the sensor. This construction maintains fast diffusion of the gas through the sensor to eliminate time delays due to the diffusion of gas through the sensor element. This is accomplished by making the sensor active material highly porous, preferably with large diameter bubbles and by maintaining the sensor relatively thin. This formation is aided by the inclusion of aluminum nitrate with 9 $H_2O$ in the composition, which forms gas bubbles on heating aiding porosity, and by controlling the temperature profile to aid porosity. In the configuration described above, the sensor preferably has a porosity such that the observed surface air bubble diameter is approxmately in the range of 0.005 to 0.055 mils with a diameter of 0.025 mils preferred. The film preferably has a thickness of 0.25–3 mils with 0.75 mils or less preferred.

The construction shown in FIG. 1, particularly with the small cross-sectional area of the sensor material and the relatively large area of the heater surface, provides uniform heating of the sensor over a broad range of temperatures, not only during manufacture but during its operating phase.

When the manufacture phase of the sensor is completed, the sensor is installed in appropriate hardware (not shown) and is ready for operation. During operation of the sensor, the heater pads are connected to an appropriate source of electrical power and the sensor pads are connected to an appropriate sensing circuit such as that shown in FIG. 5. During operation of the sensor, the sensor is heated by the heater resistor to drive off moisture and to give sufficient activation energy to the sensor material. The selection of appropriate temperature is based on the requisite energy for the sorption reaction and, as much as possible, to limit occurrence of the chemical reaction between the gas and sensor. The temperature used is preferably in excess of the boiling point of water (100° C.) and below a temperature where the oxidation of the metal would occur at a significant rate. Typically, the temperature for the chlorine sensor described above would be approximately 150° C.

As indicated previously, it is believed that a sorption phenomena is responsible for the initial rapid resistance change in the sensor. In the sorption process, the chlorine diatomic gas molecule with its high electronegativity positions itself on the surface of the material, tying up a tin and removing it from its prior hole status as part of a conductive path for electrons through the material. The sorped chlorine tin compound acts as an anti-hole, increasing resistance. The advantage of a sensor system which focuses on the sorption reaction is the speed with which the reaction occurs and the speed with which the reaction reverses itself. The completion of the sorption reaction is controlled basically by the diffusion of gas in the pores of the sensor, rather than chemical reaction of the sensor material which would occur, first at the surface, and then at deeper and deeper levels in the material. Resistance change associated with the chemical reaction of the overall material is believed to be considerably slower in both directions than the sorption process.

Figure 6:
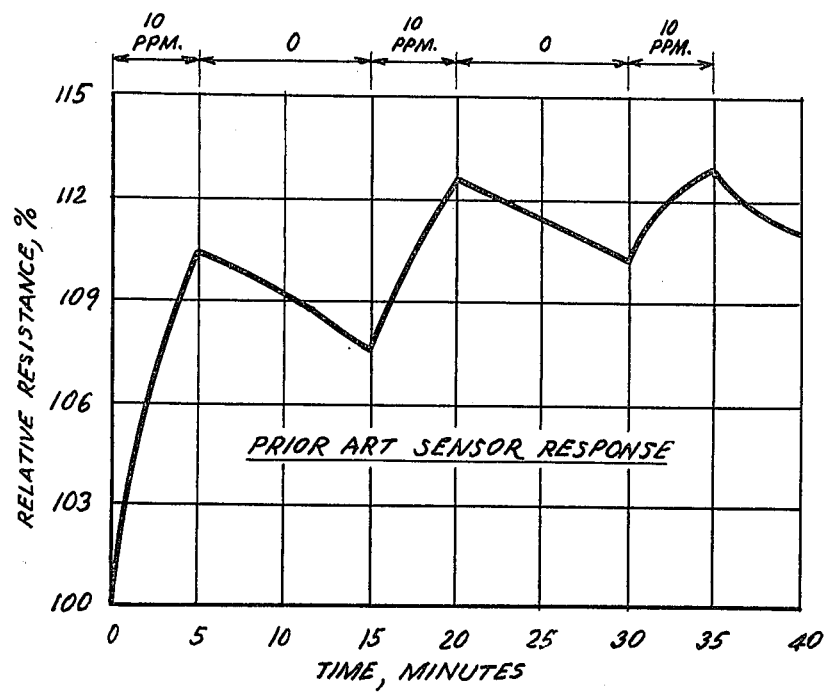
FIG. 6 is a graphic representation of a typical response in relative resistance versus time of a prior art sensor in response to the application of gas in a concentration of 10 ppm applied for five minutes, then removed for ten minutes and reapplied for five minutes, etc.
Figure 7:
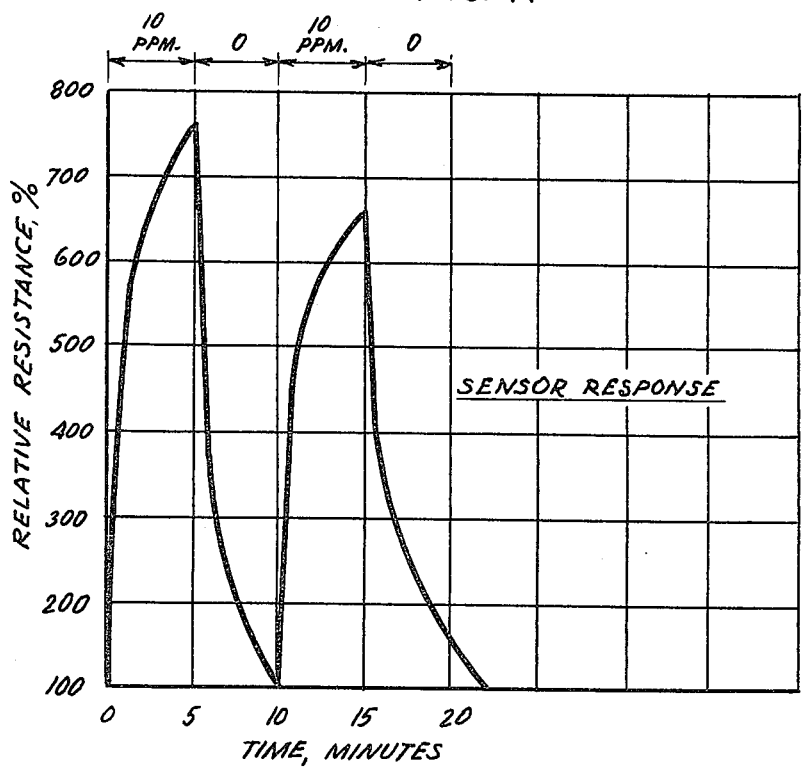
FIG. 7 is a graphical representation of the response of applicant's sensor in relative resistance versus time to the application of gas in a concentration of 10 ppm for five minutes, removed for five minutes, etc.

FIGS. 6 and 7 compare the response of a conventional chlorine gas sensor to the present chlorine sensor when exposed to the same concentration of chlorine gas, namely ten parts per million. FIG. 6 shows a typical response of a prior art sensor in this case an International Sensor Technology chlorine sensor. As will be apparent from FIG. 6, exposure to ten parts per million gas for a period of five minutes creates a relative resistance change of approximately 110% of the sensor's initial resistance value. When the chlorine gas is removed for a period of ten minutes thereafter, the sensor resistance returns to approximately 107.5% of its initial value. Additional exposure to ten parts per million chlorine gas for an additional five-minute period creates a resistance change from 107.5% of value to approximately 112.5% of value. As is apparent from FIG. 6, in the prior art sensor the relative resistance response is small; the return to normal resistance in the absence of chlorine gas proceeds slowly; and repeated exposures to the chlorine gas, even after a ten minute free interval, results in an appreciable drift of the base line of the response. This sensor exhibits a high ratio of noise to desired signal.

FIG. 7 shows the relative resistance response of applicant's chlorine sensor composed and formed as described above. As will be apparent from FIG. 7, applicant's sensor responds to the presence of chlorine in a concentration of ten parts per million by a resistance change in excess of 700% of initial value. Upon removal of chlorine gas for a period of only five minutes (half the period of FIG. 6), the sensor resistance returns rapidly to near its initial value. Upon re-exposure to chlorine in the concentration of ten parts per million for five minutes, the relative resistance of the sensor rises rapidly again to almost 700% of its initial value. In the data portrayed in FIG. 7, the second peak of resistance change is somewhat lower than the initial peak. This is due to extraneous causes in the acquisition of data represented in the figure. In the normal course, the second peak is expected to be substantially equal to the initial response.

As is apparent from FIG. 7, the response of applicant's sensor is characterized by a very substantial and very rapid resistance change within the first few seconds of exposure to the subject gas. Applicant has found that this change usually falls in the range of 10-100% resistance change for each part per million concentration of the object gas present in the atmosphere.

Figure 9:
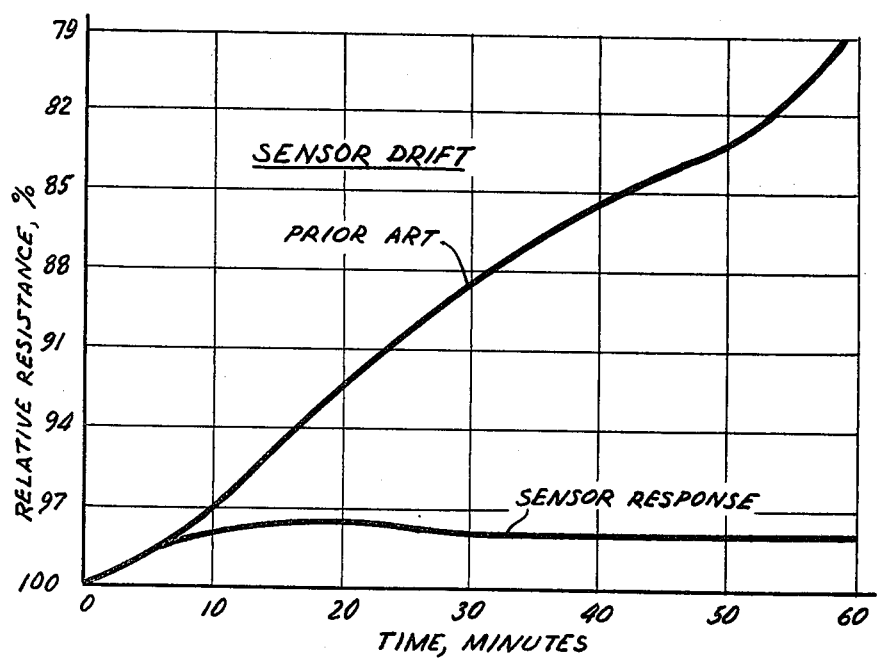
FIG. 9 is a graphical representation of typical resistance drift of applicant's sensor compared with a typical prior art sensor in relative resistance versus time beginning with turn on of the system.

FIG. 9 shows the initial sensor drift in relative resistance of applicant's sensor and a typical prior art sensor when the sensor is activated. As will be apparent from FIG. 9, applicant's sensor undergoes a very slight initial reduction in resistance upon turn-on and, after approximately 30 minutes continues at a steady, stable resistance level of greater than 97% of its initial resistance. The prior art sensor drifts during the first hour after turn-on alone to below 82% of its desired resistance level and continues to drift thereafter.

The sensing circuitry of applicant's device is designed to respond to the sharp initial changes in resistance of the gas-sensitive mass and to provide appropriate alarms and other responses in dependence on these rapid changes. Applicant has found that measurement of these rapid changes, and particularly the slope of such changes, provides a consistent and predictable measure of gas concentration, permitting evaluation of gas concentration within the early seconds of exposure to the gas.

Figure 5:
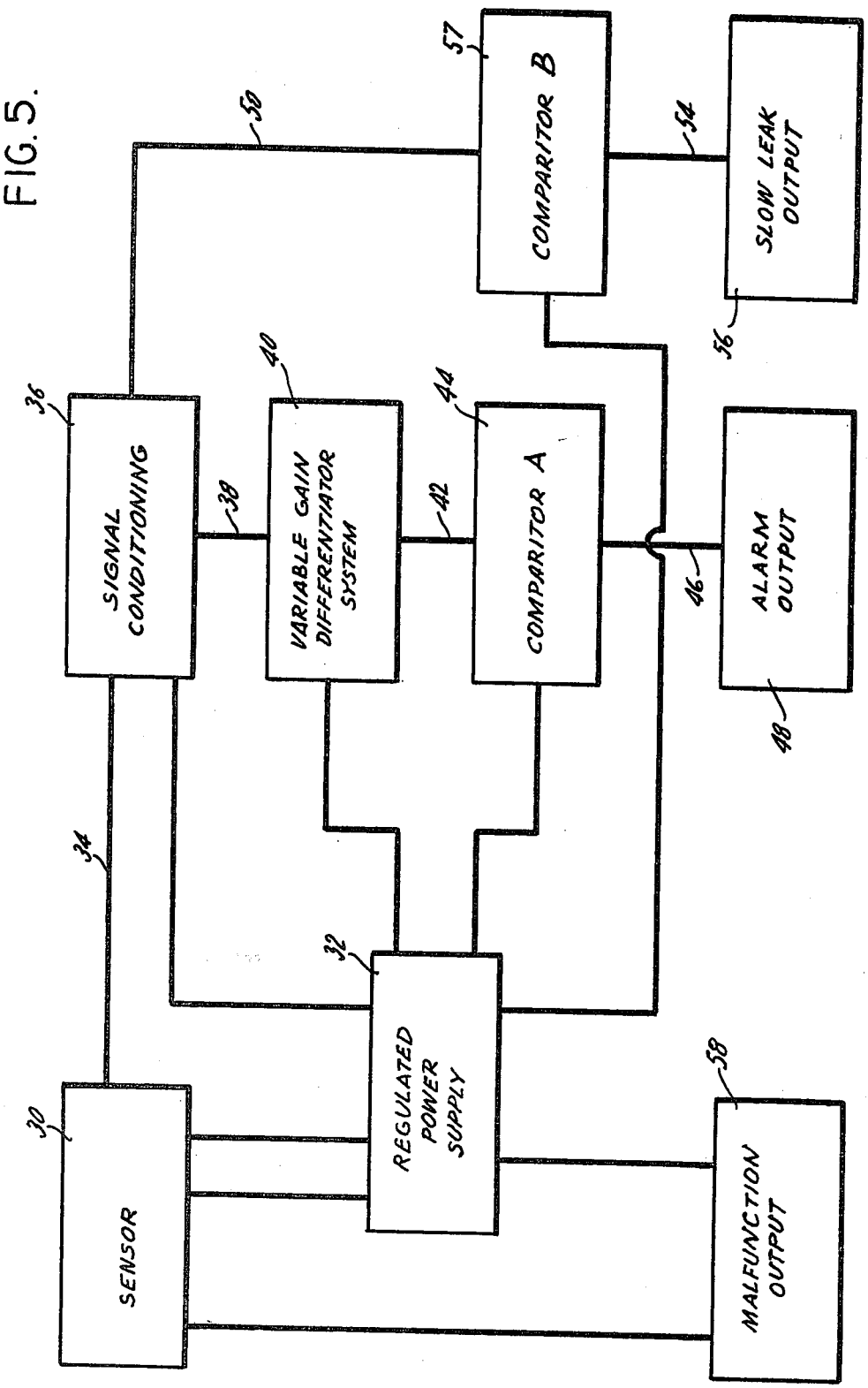
FIG. 5 is a block schematic diagram of a sensing circuit in accordance with applicant's invention.

A presently preferred embodiment of applicant's sensing and monitoring circuitry is shown in FIG. 5 in block form. It will be understood that each of the operative blocks of the circuit as shown in FIG. 5 and described below are constructed of readily available materials in accordance with circuit design techniques well known in the art. Many different specific circuits can be readily designed to incorporate the function and principles shown in FIG. 5 and described below.

The monitoring circuit operates in conjunction with the sensor 30 which is a resistive material adapted to change resistance in response to the presence of a particular gas. Preferably, the sensor is of the form described above which emphasizes initial signal response due to surface phenomena. However, a broad variety of sensors could be advantageously incorporated in conjunction with applicant's monitoring apparatus to provide improved gas monitoring performance.

Sensor 30, which for sake of discussion can be assumed to be the chloride gas sensor described above, is adapted to change resistance in response to the presence of chlorine gas in the range of zero to 100 parts per million. A typical sensor resistance change is shown, for example, in FIG. 7.

Sensor 30 is powered by a regulated power supply 32. This power supply provides power to the heater resistor to maintain the sensing material at operating temperatures. Regulated power supply 32 also provides power to the sensing element and to the electrical components of the circuit.

The sensor information signal from sensor 30 is sent over line 34 to a signal conditioning circuit 36. Signal conditioning circuit 36 matches the impedance of sensor 30 to the instrumentation and provides any required gain of signal level for convenient processing.

The conditioned sensor signal is applied through lead 38 to a variable gain differentiator system 40. Variable gain differentiator system 40 receives the conditioned sensor signal and generates an output proportional to the rate of change of the conditioned sensor input. Variable gain differentiator system 40 operates with a time constant preferably in the range of 1-15 seconds so that it looks primarily at relatively rapid change in the conditioned sensor signal. This eliminates changes in the condition sensor signal due to environmental factors such as humidity and temperature. As previously indicated, drift due to temperature, humidity, sensor aging and the like proceeds relatively slowly such that the change due to such phenomena over the sampling time interval of the variable gain differentiator system with a time constant of 1-15 seconds is characteristically very small. This differs sharply from the changes due to the presence of the gas of interest which induces a very rapid change in the conditioned sensor signal.

In general, the time constant of the circuit can be adjusted to coordinate with the sensor in use. Preferably, a time constant of ⅓ of the time to maximum slope of resistance or maximum variable gain differentiator system signal output as empirically determined for a particular group of sensors has been found appropriate. A five second time constant generally provides good results.

Figure 8:
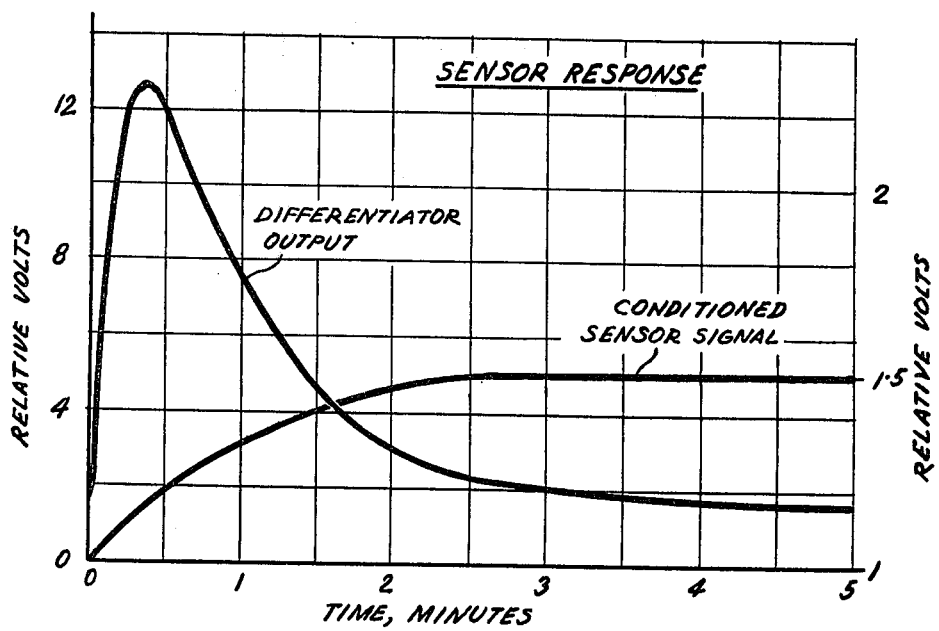
FIG. 8 is a graphic representation of the sensor output showing the conditioned sensor signal versus time (in relative volts on the right-hand scale) and the variable gain differentiator system output signal versus time (in relative volts on the left-hand scale)

FIG. 8 graphically represents a typical conditioned sensor signal of applicant's system and compares it to the output of the variable gain differentiator system 40. As is apparent from FIG. 8, on exposure to chlorine gas the conditioned sensor signal rises sharply during the first minute of exposure and then proceeds toward a steady value. The variable gain differentiator system output is proportional to the rate of change of the conditioned sensor signal and indicates a very high and immediate rise during the first 30 seconds of exposure to gas. Both curves on FIG. 8 indicate relative volts with the conditioned sensor signal being read on the right-hand scale and the differentiator output being read on the left-hand scale.

The voltage output of variable gain differentiator system 40 is applied on lead 42 to comparator A, number 44. Comparator A receives a preset, standard voltage from regulated power supply 32 which it compares to the variable gain differentiator system output. The regulated voltage applied to comparator A is determined based upon the known characteristics of the sensor and the monitoring system such that it represents a known concentration of gas.

Applicant has found that the very early initial response of applicant's sensor when viewed in terms of the rate of change of sensor signal with time responds to the presence of gas in different concentrations in a highly consistent and characteristic manner dependent on such concentration. For a specific sensor and gas, applicant has found that the maximum rate of change of signal level as represented by the output of variable gain differentiator system 40 is proportional to the concentration of gas. Applicant has also found that the maximum rate of change or maximum slope of the sensor signal output is reached very early in the sensor response time, usually within the first 30 seconds of response.

Relying on these principles, the voltage applied from regulator power supply 32 to comparator A is predetermined for a predetermined gas level. When the variable gain differentiator output on line 42 exceeds the regulated control voltage, a signal is provided on lead 46 to an alarm output 48.

It will be understood that the voltage increase in the output of variable gain differentiator system 40 may be relatively transient so that the comparator 44 or alarm output 48 preferably include a latch system such that once the comparison voltage is equaled, the alarm continues either for some prescribed period before an automatic reset or until a manual reset is accomplished. Latch systems for providing this function are well known in the art and need not be described here in detail.

In addition to monitoring the variable gain differentiator system output signal, applicant's system also directly monitors the conditioned sensor signal from signal conditioning circuit 36, which is delivered on lead 50 to a second comparator, comparator B, number 57. This monitoring of the condition sensor signal is designed to detect slow leak type phenomena wherein gas concentration may increase from very, very low levels to potentially dangerous levels very slowly over a long period of time. Comparator B constantly compares the conditioned signal level with a signal delivered from the regulated power supply which is preestablished to be indicative of presence of undesirable levels of gas. If the signal on lead 50 exceeds the selected voltage applied to comparator B, comparator B puts an output signal on lead 54 which activates slow leak alarm circuit 56. Here again, as in the case of alarm circuit 48, a latching circuit with automatic or manual reset is desirable.

In addition to the alarm and slow leak outputs, applicant's circuit is designed to provide a malfunction indication. To this end, a malfunction output circuit 58 is provided which responds to a change of sensor resistance outside of a preset normal range, the normal range preferably being approximatey 500–20,000 ohms. The manfunction alarm is also adapted to respond to severe variations in the heater resistor voltage, indicative of short or open circuits in the heater resistor. Malfunction output 58 may also incorporate an appropriate latch system.

Applicant's sensor system has been described primarily as it applies to the sensing of chlorine gas using a tin, tin oxide sensor element. However, the principles of applicant's invention are applicable to other metal, metal oxide systems, particularly systems incorporating titanium, iron, tantalum, zirconium, paladium or tungsten. The selection of the metals is a function of the gas that is desired to be measured. As a general rule, the sum of the electronegativity with a sign change of the gas and the electropositivity of the metal should be above 2.5 electron volts. Tin with 1.8 electron volts is highly attracted to chlorine with 3.15. For other gases to be measured that are lower in electronegativity, a metal with higher electropositivity would be selected.

It should also be understood that while applicant's sensor formation and construction is adapted to respond primarily to a selected gas such as chlorine it may also partially respond to other gases. Applicant has found that the undesirable response of the chlorine sensor described above to interfering gases is considerably lower than that normally associated with gas sensors of the solid-state type. Only hydrogen dioxide provides a substantial sensor output. Applicant's chlorine sensor does not response adversely to water, sulphur dioxide, oxygen, ammonia, carbon monoxide or many other gases which may interfere with prior chlorine sensors.

It will be appreciated that the above disclosure emphasizes the presently preferred embodiment of the present invention, but that numerous other embodiments, including those directed to different gases and incorporating different metal, metal-oxide systems, will be immediately apparent to those skilled in the art based on the foregoing disclosure without departing from the spirit or scope of applicant's invention as defined in the following claims.

What is claimed is:

1. A gas sensor which is adapted to change electrical resistance in response to the presence of a gas comprising a metal, an oxide of said metal and an inert support material, all said constituents being formed together into a porous mass.

2. A gas sensor in accordance with claim 1 wherein said metal is selected from the group consisting of tin, titanium, iron, tantalum, zirconium, palladium and tungsten.

3. A gas sensor in accordance with claim 1 further including as a constituent of the gas sensor a compound of said metal and the gas which the sensor is adapted to sense so that said sensor composition is poised by a reverse concentration driving force to resist chemical reaction between said composition and the object gas.

4. A gas sensor in accordance with claim 1 further including means for providing heat to said gas sensor.

5. A gas sensor in accordance with claim 4 wherein said heat providing means is adapted to provide sufficient activation energy for the sorption of said gas on said material but insufficient activation energy to encourage the chemical reaction of said gas with said material.

6. A gas sensor in accordance with claim 4 further including a heat sink which provides a reservoir of thermal energy for said sensor material during exposure to said gas.

7. A gas sensor which is adapted to change electrical resistance in response to the presence of chlorine gas comprising tin, an oxide of tin and an inert support material, all formed into a porous mass, metallic tin constituting between 50 and 95 weight percent of said mass.

8. A gas sensor which is adapted to change electrical resistance in response to the presence of chlorine gas comprising tin, an oxide tin, and stannic chloride.

9. A gas sensor in accordance with claim 8 wherein said tin constitutes 50-95 weight percent of the gas sensor.

10. A gas sensor in accordance with claim 8 further including an inert support material, wherein said tin, oxide of tin, stamic chloride and inert support material are constituted as a porous mass.

11. A gas sensor comprising a substrate, a layer of resistance material deposited on said substrate so as to form a heater resistor adapted to make electrical contact with a source of electrical power, a layer of non-porous electrically non-conductive material deposited on said heater resistor and in thermal communication therewith, the surface of said electrically non-conductive layer away from said heater resistor forming a surface electrically insulated from said heater resistor, a pair of conductive contacts associated with said surface and defining a gap on said surface between said contacts, and a gas responsive material which changes electrical resistance in response to the presence of gas deposited in said gap on said surface in electrical communication with said contacts, application of electrical power to said heater resistor heating said gas sensing material.

12. A gas sensor in accordance with claim 11 wherein the area of said heater resistor is large with respect to the area of said gap to insure uniform heating.

13. Apparatus in accordance with claim 11 wherein the width of said gap is less than 4 mils.

14. Apparatus in accordance with claim 11 wherein said heating resistor comprises a substrate, a plurality of electrically conductive contacts deposited on said substrate and a resistance material deposited on said substrate intermediate said contacts.

15. Apparatus in accordance with claim 11 further including a heat sink for providing a reservoir of heat for said gas responsive material.

16. A gas sensing material comprising a metal and an oxide of said metal, said metal comprising 50-95 weight percent of said material, said material exhibiting a reversible change in relative resistance in response to the presence of gas in excess of ten percent for each part per million gas present.

* * * * *